United States Patent [19]

Tanaka et al.

[11] Patent Number: 4,814,523
[45] Date of Patent: Mar. 21, 1989

[54] NEMATIC LIQUID CRYSTAL COMPOUND OF FOUR RING SYSTEMS

[75] Inventors: Yasuyuki Tanaka; Haruyoshi Takatsu; Kiyohumi Takeuchi, all of Tokyo; Yuji Tamura, Saitama, all of Japan

[73] Assignee: Dainippon Ink and Chemicals, Inc., Tokyo, Japan

[21] Appl. No.: 195,326

[22] Filed: May 18, 1988

[30] Foreign Application Priority Data

May 19, 1987 [JP] Japan .................................. 62-120071

[51] Int. Cl.$^4$ .......................... C02F 1/13; C09K 19/30; C07C 25/18
[52] U.S. Cl. .................. 570/129; 252/229.5; 252/299.63; 350/350 R; 350/350 S
[58] Field of Search .................. 252/299.63, 299.5; 350/350 S, 350 R; 570/129, 182, 130, 188

[56] References Cited

U.S. PATENT DOCUMENTS

| | | | |
|---|---|---|---|
| 4,405,488 | 9/1983 | Sugimori et al. | 252/299.63 |
| 4,415,470 | 11/1983 | Eidenschime et al. | 252/299.63 |
| 4,439,340 | 3/1984 | Kojoma et al. | 252/299.63 |
| 4,472,293 | 9/1984 | Sugimori et al. | 252/299.63 |
| 4,477,369 | 10/1984 | Sugimori et al. | 252/299.63 |
| 4,502,974 | 3/1985 | Sugimori et al. | 252/299.63 |
| 4,545,922 | 10/1985 | Eidenschime et al. | 252/299.63 |
| 4,683,078 | 7/1987 | Sugimori et al. | 252/299.63 |

Primary Examiner—Teddy S. Gron
Attorney, Agent, or Firm—Armstrong, Nikaido, Marmelstein & Kubovcik

[57] ABSTRACT

A tetracyclic nematic liquid crystal compound of the following formula:

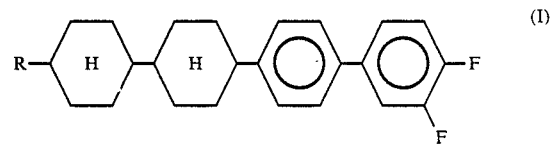

wherein R represents a straight-chained alkyl group carrying one to seven carbon atoms; and

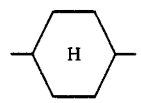

has a trans (equatorial-equatorial) configuration; is disclosed. This compound has a high N-I transition temperature and a low S-N transition temperature and is highly useful as an electro-optical display material.

3 Claims, No Drawings

NEMATIC LIQUID CRYSTAL COMPOUND OF FOUR RING SYSTEMS

BACKGROUND OF THE INVENTION

1. Field of the Invention

This invention relates to a nematic liquid crystal compound of four ring systems useful as an electro-optical display material.

2. Prior Art

Typical liquid crystal display cells include a field-effect mode cell proposed by M. Schadt et al. (cf. Appld. Phys. Letters, 18, 127–128 (1971)), a dynamic scattering mode cell proposed by G.H. Heilmeier et al. (cf. Proc. of the I.E.E.E., 56, 1162–1171 (1968)) and a guest-host mode cell proposed by G.H. Heilmeier et al. (cf. Appld. Phy. Letters, 13, 91 (1968)) or D.L. White et al. (J. of Appld. Phys., 45, 4718 (1974)).

Among various requirements for these liquid crystal display cells, it is a commonly important one to have a nematic phase over a wide range of temperature involving room temperature. Many of commercially feasible liquid crystal materials available today are usually prepared by mixing a few or more components made of a compound having a nematic phase at or around room temperature and another one having a nematic phase within a temperature range higher than room temperature. Most of these mixed liquid crystals commercially used today are required to have a nematic phase over the full temperature range of −50° to +65° C. In order satisfy these requirements, compounds having a crystalline to nematic (C-N) transition temperature of approximately 100° C. and a nematic to isotropic (N-I) transition temperature of approximately 200° C., for example, 4,4″-substituted terphenyl, 4,4′-substituted biphenylcyclohexane or phenyl 4,4′-substituted benzoyloxybenzoate are frequently employed as the compound having a nematic phase within a temperature range higher than room temperature. Recently there are required liquid crystal materials having a nematic phase within a further higher temperature range. This requirement is satisfied by providing a compound having an N-I transition temperature as high as approximately 300° C.

Prior known compounds similar to the compound of this invention are disclosed in Japanese Patent Application (OPI) No. 92228/85 (the term "OPI" refers to unexamined published Japanese patent application), and U.S. Pat. No. 4,472,293.

However these compounds usually have a disadvantage that each has a smectic phase and a high smectic to nematic (S-N) transition temperature which corresponds to the lower limit of the nematic phase temperature range. When a compound having a high S-N transition temperature is added to mixed nematic liquid crystals, which are widely used at present as a liquid-crystal host, to thereby elevate the N-I transition temperature of the mixed liquid crystals, the resulting mixture is undesirable in having a smectic phase within a low temperature range.

SUMMARY OF THE INVENTION

It is an object of the present invention to provide a novel nematic liquid crystal compound having a high N-I transition temperature and a low S-N transition temperature.

In order to overcome the above-mentioned problems, the present invention provides a compound of the following general formula (I):

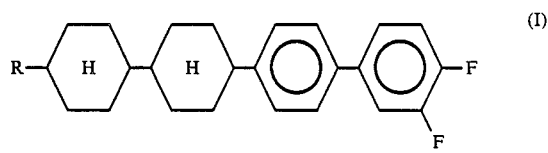

wherein R represents a straight-chained alkyl group carrying one to seven carbon atoms; and

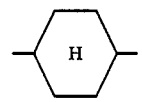

has a trans (equatorial-equatorial) configuration.

DETAILED DESCRIPTION OF THE INVENTION

The compound (I) according to the present invention may be prepared by the following method.

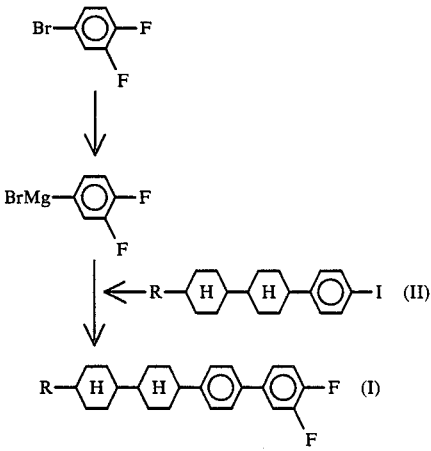

wherein R is as defined above.

1-Bromo-3,4-difluorobenzene is reacted with magnesium in an organic solvent such as dry ether or dry tetrahydrofuran to thereby give a Grignard reagent. Then the Grignard reagent is reacted with the compound (II) in the presence of a catalyst such as palladium (II) chloride. Thus the compound (I) of the present invention is prepared.

The transition temperatures of typical compounds of the formula (I) thus obtained are shown in Table 1.

TABLE 1

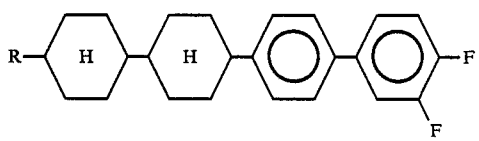

| No. | R | Transition Temperature (°C.)* |
|-----|---|-------------------------------|
| 1 | n-C$_3$H$_7$— | 90 (C ⟶ N) |
| | | 88 (N ⇌ S) |

TABLE 1-continued

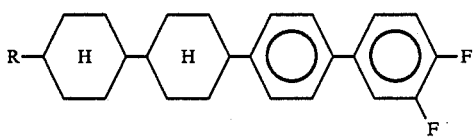

| No. | R | Transition Temperature (°C.)* |
|---|---|---|
| 2 | n-C₄H₉— | 291 (N ⇌ I) |
| | | 65 (C → S) |
| | | 105 (S ⇌ N) |
| | | 291 (N ⇌ I) |

*Remarks:
C: crystalline phase; S: smectic phase;
N: nematic phase; and I: isotropic liquid phase.

All of the compounds of formula (I) in accordance with this invention show weak positive dielectric anisotropy. Most of them are nematic liquid crystalline compounds, and some of them are compounds similar to liquid crystals. Accordingly, they can be used, for example, in the form of a mixture with other nematic liquid crystalline compounds having negative or weakly positive dielectric anisotropy, as a material for dynamic scattering mode display cells. Furthermore, as a mixture with other nematic liquid crystalline compounds having strong positive dielectric anisotropy, they can be used as a material for field effect mode display cells.

Typical examples of preferred nematic liquid crystalline compounds which can be used as mixtures with the compounds of general formula (I) include 4'-substituted phenyl 4-substituted benzoate, 4'-substituted phenyl 4-substituted cyclohexanecarboxylate, 4'-substituted biphenyl 4-substituted cyclohexanecarboxylate, 4'-substituted phenyl 4-(4-substituted cyclohexanecarbonyloxy)benzoate, 4'-substituted phenyl 4-(4-substituted cyclohexyl)benzoate, 4'-cyclohexyl 4-(4-substituted cyclohexyl)benzoate, 4-substituted 4'-substituted biphenyl, 4-substituted phenyl-4'-substituted cyclohexane, 4-substituted 4''-substituted terphenyl, 4-substituted biphenyl 4'-substituted cyclohexane and 2-(4-substituted phenyl)-5-substituted pyrimidine.

Table 2 lists the S-N and N-I transition temperature of known compounds similar to the compound (I) of the present invention.

TABLE 2

| Cpd. | Formula | S—N (°C.) | N—I (°C.) |
|---|---|---|---|
| (a) | n-C₃H₇—(H)—(H)—(○)—(○)—F (Japanese Patent Application (OPI) No. 92228/85) | 190 | >300 |
| (b) | n-C₃H₇—(H)—(H)—(H)—(○)—F (U.S. Pat. No. 4,472,293) | 238 | 278 |
| (c) | n-C₄H₉—(H)—(H)—(H)—(○)—F, F | 217 | 299 |

TABLE 2-continued

| Cpd. | Formula | S—N (°C.) | N—I (°C.) |
|---|---|---|---|
| | (U.S. Pat. No. 4,472,293) | | |

The composition of the known compounds (a) and (b) and the compound No. 1 of the present invention and that of the known compound (c) and the compound No. 2 of the present invention obviously indicate that each compound of the present invention has an N-I transition temperature comparable to those of known ones, i.e., approximately 300° C. as well as an S-N transition temperature significantly lower than those of the known ones.

EXAMPLE 1

5.0 g (0.026 mole) of 1-bromo-3,4-difluorobenzene was dissolved in 2 ml of dry tetrahydrofuran, which will be abbreviated as tetrahydrofuran (THF) hereinafter. The resulting solution was added dropwise to 0.69 g (0.028 gram atom) of powdery magnesium at 20° to 30° C. under stirring. The resulting mixture was further reacted at room temperature (25° C.) for three hours to thereby give a Grignard reagent.

Then 4.9 g (0.012 mole) of a compound of the formula:

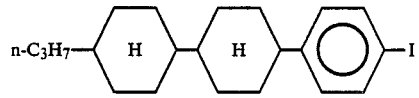

was dissolved in 10 ml of dry THF. Then the Grignard reagent as prepared above was added thereto. 5 ml of a saturated solution of PdCl₂ in dry THF was further added thereto and the resulting mixture was allowed to react at the refluxing temperature under stirring for five hours.

After cooling, the reaction mixture was added to cold dilute hydrochloric acid and the reaction product was extracted with toluene. The extract was washed with acidic sodium sulfite and the iodine thus liberated was removed. The residue was further washed with water and dried and the solvent was distilled off. The crude product thus obtained was purified by recrystallizing from n-hexane. Thus 2.8 g (0.0071 mole) of the following compound was obtained.

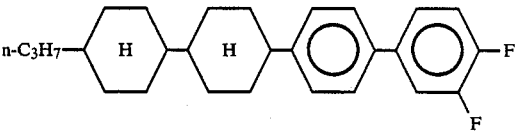

Yield: 59%.
Transition temperature:
90° C. (C→N),
88° C. (N→←S), and
291° C. (N→←I).

EXAMPLE 2

The procedure of Example 1 was followed by thereby give the the following compound.

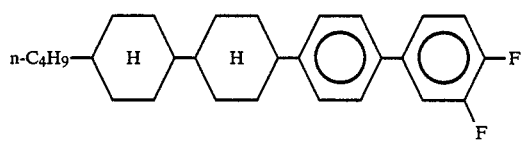

Yield: 61%.
Transition temperature:
65° C. (C→S),
105° C. (S→←N), and
291° C. (N→←I).

The compound of the present invention has a high N-I transition temperature as well as a low S-N transition temperature. Thus it may be mixed with nematic liquid crystals, which are widely employed as a liquid crystal host at present, thus elevating the N-I transition temperature of the mixed liquid crystals and preventing the mixed liquid crystals from exhibiting a smectic phase within a low temperature range.

While the invention has been described in detail and with reference to specific embodiments thereof, it will be apparent to one skilled in the art that various changes and modifications can be made therein without departing from the spirit and scope thereof.

What is claimed is:

1. A compound of the general formula:

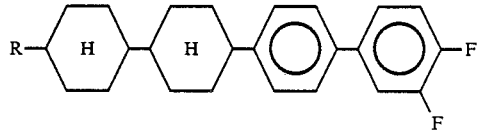

wherein R represents a straight-chained alkyl group carrying one to seven carbon atoms; and

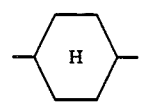

has a trans (equatorial-equatorial) configuration.

2. The compound of claim 1 represented by the formula:

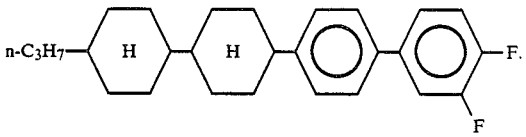

3. The compound of claim 1 represented by the formula

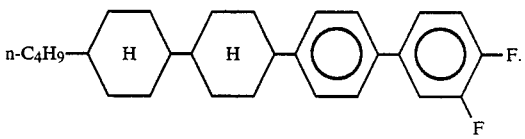

* * * * *